US00PP15460P2

(12) United States Plant Patent
Hofmann

(10) Patent No.: US PP15,460 P2
(45) Date of Patent: Jan. 4, 2005

(54) **NEW GUINEA *IMPATIENS* PLANT NAMED 'FISNICS SWEET RED'**

(50) Latin Name: *Impatiens hawkeri*
Varietal Denomination: Fisnics Sweet Red

(76) Inventor: Birgit Christa Hofmann, Gassenweg 29, 56170 Bendorf (DE)

( * ) Notice: Subject to any disclaimer, the term of this patent is extended or adjusted under 35 U.S.C. 154(b) by 99 days.

(21) Appl. No.: 10/452,973

(22) Filed: Jun. 3, 2003

(51) Int. Cl.[7] ..... A01H 5/00

(52) U.S. Cl. ..... Plt./318
(58) Field of Search ..... Plt./318

*Primary Examiner*—Bruce R. Campell
*Assistant Examiner*—Susan B. McCormick
(74) *Attorney, Agent, or Firm*—C. A. Whealy

(57) ABSTRACT

A new and distinct cultivar of New Guinea *Impatiens* plant named 'Fisnics Sweet Red', characterized by its outwardly spreading and uniformly mounded plant habit; medium growth habit; freely branching and freely flowering habit; dark green-colored foliage; and medium to large, rounded, light pink and red bi-colored flowers that are positioned above and beyond the foliage.

1 Drawing Sheet

Botanical classification/cultivar designation: *Impatiens hawkeri* cultivar Fisnics Sweet Red.

BACKGROUND OF THE INVENTION

The present Invention relates to a new and distinct cultivar of New Guinea *Impatiens* plant, botanically known as *Impatiens hawkeri*, and hereinafter referred to by the name 'Fisnics Sweet Red'.

The new *Impatiens* is a product of a planned breeding program conducted by the Inventor in Hillscheid, Germany and Moncarapacho, Portugal. The objective of the breeding program is to develop new medium-sized *Impatiens* cultivars with an early to medium flowering response and large rounded flowers with attractive coloration.

The new *Impatiens* originated from a cross-pollination made by the Inventor during the summer of 1998 of the *Impatiens hawkeri* cultivar Alexis, disclosed in U.S. Plant patent application Ser. No. 09/765,324, abandoned, as the female, or seed, parent with a proprietary seedling selection of *Impatiens hawkeri* identified as code number K98-4090-11, not patented, as the male, or pollen, parent. The cultivar Fisnics Sweet Red was discovered and selected by the Inventor as a flowering plant within the progeny of the stated cross-pollination in a controlled environment in Moncarapacho, Portugal in April, 1999.

Asexual reproduction of the new cultivar by terminal cuttings taken in Moncarapacho, Portugal, since July, 1999, has shown that the unique features of this new *Impatiens* are stable and reproduced true to type in successive generations.

SUMMARY OF THE INVENTION

The following traits have been repeatedly observed and are determined to be the unique characteristics of 'Fisnics Sweet Red'. These characteristics in combination distinguish 'Fisnics Sweet Red' as a new and distinct *Impatiens* cultivar:

1. Outwardly spreading and uniformly mounded plant habit; medium growth habit.
2. Freely branching and freely flowering habit.
3. Dark green-colored foliage.

4. Medium to large, rounded, light pink and red bi-colored flowers that are positioned above and beyond the foliage.

Plants of the new *Impatiens* can be compared to plants of the female parent, the cultivar Alexis. In side-by-side comparisons conducted by the Inventor in Hillscheid, Germany, plants of the new *Impatiens* differed from the plants of the Alexis in the following characteristics:

1. Plants of the new *Impatiens* were larger and more vigorous than plants of the Alexis.
2. Plants of the new *Impatiens* had larger and lighter green-colored leaves than plants of the cultivar Alexis.
3. Plants of the new *Impatiens* and the cultivar Alexis differed in flower coloration.

Plants of the new *Impatiens* can be compared to plants of the male parent selection. In side-by-side comparisons conducted by the Inventor in Hillscheid, Germany, plants of the new *Impatiens* differed from plants of the male parent selection in the following characteristics:

1. Plants of the new *Impatiens* were shorter and denser than plants of the male parent selection.
2. Leaves of plants of the new *Impatiens* were slightly lighter green in color than leaves of plants of the male parent selection.
3. Plants of the new *Impatiens* and the male parent selection differed in flower coloration.

Plants of the new *Impatiens* can also be compared to plants of the cultivar Neptis, disclosed in U.S. Plant Pat. No. 10,321. In side-by-side comparisons conducted by the Inventor in Hillscheid, Germany, plants of the new *Impatiens* differed from plants of the cultivar Neptis in the following characteristics:

1. Plants of the new *Impatiens* were shorter than plants of the cultivar Neptis.
2. Leaves of plants of the new *Impatiens* were narrower and darker green in color than leaves of plants of the cultivar Neptis.
3. Plants of the new *Impatiens* had larger flowers than plants of the cultivar Neptis.
4. Plants of the new *Impatiens* and the cultivar Neptis differed slightly in flower coloration.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the colors of the new *Impatiens*. The photograph comprises a side perspective view of a typical flowering plant of 'Fisnics Sweet Red' grown in a container.

DETAILED BOTANICAL DESCRIPTION

The cultivar Fisnics Sweet Red has not been observed under all possible environmental conditions. The phenotype may vary somewhat with variations in environment such as temperature and light intensity, without, however, any variance in genotype.

The aforementioned photograph, following observations and measurements describe plants grown in Hillscheid, Germany, under commercial production practice in a glass-covered greenhouse. Rooted young plants were planted in 12-cm containers in late February and the aforementioned photograph and following observations and measurements were taken about 11 weeks later in early May. During the production of the plants, day temperatures were about 18 to 22° C. and night temperatures were about 16 to 18° C. In the following description, color references are made to The Royal Horticultural Society Colour Chart, 1995 Edition, except where general terms of ordinary dictionary significance are used.

Botanical classification: *Impatiens hawkeri* cultivar Fisnics Sweet Red.

Parentage:

*Female parent.*—*Impatiens hawkeri* cultivar Alexis, disclosed in U.S. Plant patent application Ser. No. 09/765,324.

*Male parent.*—Proprietary seedling selection of *Impatiens hawkeri* identified as code number K98-4090-11, not patented.

Propagation:

*Type cutting.*—Terminal tip cuttings.

*Time to initiate roots.*—Summer: About 8 to 10 days at 24° C. Winter: About 12 to 15 days at 21° C.

*Time to produce a rooted cutting.*—Summer: About 15 days at 24° C. Winter: About 18 to 20 days at 21° C.

*Root description.*—Numerous, fibrous, and freely branching; 158D to 179D in color.

Plant description:

*General appearance.*—Outwardly spreading and uniformly mounded plant growth habit; medium growth habit; freely branching habit; bushy appearance; freely flowering. Moderately vigorous.

*Crop time.*—From a rooted cutting, about 9 to 10 weeks are required to produce finished flowering plants in 12-cm containers.

*Plant height.*—About 20.5 cm.

*Plant diameter or spread.*—About 40 to 45 cm.

*Lateral branches.*—Quantity per plant: About 9 to 11. Length: About 16 to 18 cm. Diameter: About 6 to 7 mm. Internode length: About 5 to 7 cm. Texture: Smooth, glabrous. Color: 185A.

*Foliage description.*—Arrangement: Primarily in whorls. Length: About 13.5 to 14.5 cm. Width: About 4.5 to 5 cm. Shape: Elliptic. Apex: Acute to acuminate. Base: Acute. Margin: Serrulate with ciliation. Texture: Smooth, occasionally somewhat rugose; glabrous. Color: Developing foliage, upper surface: 139A. Developing foliage, lower surface: 185B to 185C. Fully expanded foliage, upper surface: 139A. Fully expanded foliage, lower surface: Purple, 185B to 185C, and green, 138A, marbled. Venation, upper surface: 53C. Venation, lower surface: 187B. Petiole: Length: About 1 to 1.5 cm. Diameter: About 3 mm. Texture: Smooth, glabrous. Color, upper surface: 53C to 53D. Color, lower surface: 185A.

Flower description:

*Flower type and flowering habit.*—Single, medium to large, rounded, light pink and red bi-colored flowers. Freely and continuously flowering; usually about 7 to 9 flowers and flower buds per lateral branch. Flowers positioned above and beyond the foliage; flowers typically face parallel to the leaf canopy. Petals not persistent; gynoecium persistent. Flowers not fragrant.

*Flower longevity.*—Flowers last about 8 to 9 days on the plant.

*Flowering season.*—Year-round under greenhouse conditions. Plants begin flowering about 9 to 9.5 weeks after planting.

*Flower bud.*—Length: About 2.1 cm. Diameter: About 1.6 cm. Shape: Ovoid. Color: 50A.

*Flower length.*—About 6.3 to 6.5 cm.

*Flower width.*—About 6.3 to 6.5 cm.

*Flower depth.*—About 1 cm.

*Petals.*—Quantity: Five per flower, imbricate. Length: Banner petals: About 2.4 to 2.6 cm. Lateral and base petals: About 3 cm. Width: Banner petal: About 4 to 4.5 cm. Lateral and base petals: About 3.5 to 4.5 cm. Shape: Cordate. Apex: Weakly lobed. Base: Attenuate. Margin: Entire. Aspect: Mostly flat. Texture: Smooth; satiny. Color: When opening, upper surface: 46C. When opening, lower surface: 50A to 50B. Fully opened, upper surface: Ground color, 56C; banner petals, towards base and central stripes on lateral and base petals, 46C. Fully opened, lower surface: 50B.

*Spur.*—Quantity: One per flower. Length: About 4.8 to 5.2 cm. Diameter: At apex: About 0.5 mm. At flower: About 2 to 3 mm. Aspect: Curved. Color: Towards base, 53D; towards apex, 144B.

*Peduncles.*—Length: About 5.5 to 6 cm. Diameter: About 2 mm. Texture: Smooth, glabrous. Strength: Strong, flexible. Color: 144D.

*Reproductive organs.*—Androecium: Stamen number: Five fused at anthers, hooded; filaments free. Anther length: About 5 to 6 mm. Anther shape: Obovate. Anther color: 8D; spot, 52B. Pollen amount: Moderate. Pollen color: 8D. Gynoecium: Pistil quantity: One per flower. Pistil length: About 5 to 6 mm. Stigma color: Close to 53A. Style color: 53A. Ovary: Five-celled. Ovary color: 187A.

*Seed/fruit.*—Seed and fruit development has not been observed.

Disease/pest resistance: Plants of the new *Impatiens* have not been observed to be resistant to pathogens and pests common to *Impatiens*.

Low temperature tolerance: Plants of the new *Impatiens* have been observed to tolerate night temperatures of 5° C. with 10° C. day temperatures.

It is claimed:

1. A new and distinct cultivar of New Guinea *Impatiens* plant named 'Fisnics Sweet Red', as illustrated and described.

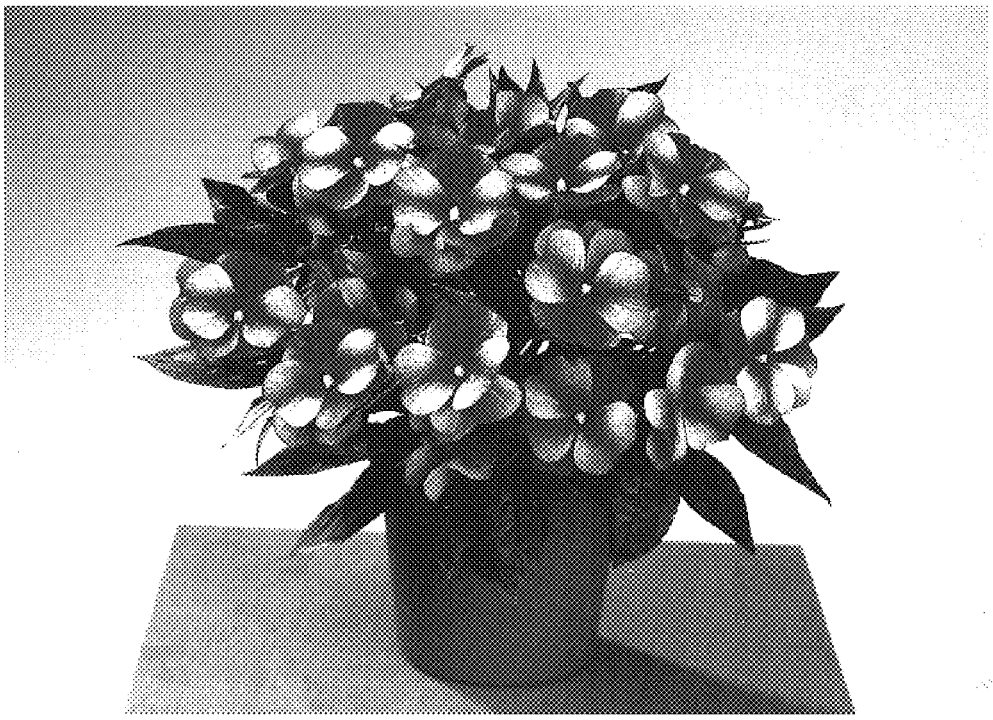

* * * * *